US012589418B2

(12) United States Patent
Kelley et al.

(10) Patent No.: US 12,589,418 B2
(45) Date of Patent: Mar. 31, 2026

(54) AUTOMATED DEVICE CLEANING AND TRANSFERRING SYSTEMS AND METHODS

(71) Applicant: Universal City Studios LLC, Universal City, CA (US)

(72) Inventors: Sarah Anne Kelley, Orlando, FL (US); Matthew Paul Meyer, Orlando, FL (US); Daniel Matthew Freedman, Orlando, FL (US); Clifton Amir Montgomery, Windermere, FL (US)

(73) Assignee: Universal City Studios LLC, Universal City, CA (US)

( * ) Notice: Subject to any disclaimer, the term of this patent is extended or adjusted under 35 U.S.C. 154(b) by 72 days.

(21) Appl. No.: 18/139,832

(22) Filed: Apr. 26, 2023

(65) Prior Publication Data

US 2024/0359217 A1     Oct. 31, 2024

(51) Int. Cl.
*A61L 2/04*          (2006.01)
*A61L 2/10*          (2006.01)
(Continued)

(52) U.S. Cl.
CPC ................ *B08B 3/041* (2013.01); *A61L 2/04* (2013.01); *A61L 2/10* (2013.01); *B08B 7/0057* (2013.01); *B08B 7/0071* (2013.01); *B08B 7/04* (2013.01); *B65G 15/00* (2013.01); *B65G 2811/095* (2013.01)

(58) Field of Classification Search
CPC ............. B65G 2811/095; A47L 15/242; A47L 15/24–245
See application file for complete search history.

(56) References Cited

U.S. PATENT DOCUMENTS

| | | | |
|---|---|---|---|
| 2,971,634 A | 2/1961 | Wilde et al. | |
| 6,223,502 B1 * | 5/2001 | Cress ................... | A47L 15/247 |
| | | | 53/167 |

(Continued)

FOREIGN PATENT DOCUMENTS

| | | | | |
|---|---|---|---|---|
| JP | H10185841 A | * | 7/1998 | |
| KR | 20090113060 A | * | 10/2009 | |
| WO | WO2022147059 A1 | * | 7/2022 | |

OTHER PUBLICATIONS

PCT/US2024/025232 International Search Report and Written Opinion mailed Jul. 5, 2024.

(Continued)

*Primary Examiner* — Kaj K Olsen
*Assistant Examiner* — Richard Z. Zhang
(74) *Attorney, Agent, or Firm* — Fletcher Yoder, P.C.

(57) ABSTRACT

A method of operating a cleaning and transferring system in a venue with a first location and a second location includes receiving one or more accessories onto a conveyor at the second location. The method also includes transferring the one or more accessories from the second location to the first location via the conveyor. The method further includes cleaning the one or more accessories during the transferring of the one or more accessories from the second location to the first location via the conveyor. The method further includes receiving one or more guest items onto the conveyor at the first location. The method further includes transferring the one or more guest items from the first location to the second via the conveyor.

11 Claims, 5 Drawing Sheets

(51) Int. Cl.

| | | |
|---|---|---|
| *B08B 3/04* | (2006.01) | |
| *B08B 7/00* | (2006.01) | |
| *B08B 7/04* | (2006.01) | |
| *B65G 15/00* | (2006.01) | |

(56) References Cited

U.S. PATENT DOCUMENTS

| | | | |
|---|---|---|---|
| 9,617,082 B2 | 4/2017 | Baker | |
| 10,376,605 B1 | 8/2019 | Majdali et al. | |
| 10,682,989 B2 | 6/2020 | Blackstock | |
| 10,905,307 B2 | 2/2021 | Yoon et al. | |
| 2006/0158043 A1 | 7/2006 | Brouwer et al. | |
| 2010/0043834 A1 | 2/2010 | Scheringer | |
| 2013/0240001 A1 | 9/2013 | Padtberg et al. | |
| 2020/0153284 A1* | 5/2020 | Shi ........................... H02J 7/02 | |
| 2021/0138965 A1 | 5/2021 | Ugrin et al. | |

OTHER PUBLICATIONS

White Designs Conveyor System Ready for Germicidal Lamps to Sterilize Uniforms and Personal Property, White Conveyor—Markets, Apr. 15, 2020, 3 pages, https://www.white-conveyors.com/trends.php?id=2.

Watch the Avtec Bus Trac Conveyor in Action, Unified Brands—News and Insights, accessed Apr. 26, 2023, 2 pages, https://unifiedbrands.net/watch-the-avtec-bus-trac-conveyor-in-action/.

Slat Belt Conveyor, Unified Brands-Equipment by Brand, accessed Apr. 26, 2023, 3 pages, https://unifiedbrands.net/products/slat-belt-conveyor/.

\* cited by examiner

AUTOMATED DEVICE CLEANING AND TRANSFERRING SYSTEMS AND METHODS

BACKGROUND

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not as admissions of prior art.

Various environments, including various entertainment environments (e.g., amusement parks, theatres, restaurants), enable guests to contact and/or carry certain components within the environments. For example, guests may contact and/or carry viewing glasses in amusement parks or in theatres, and guests may contact and/or carry cutlery in restaurants. In some cases, such contact may cause bacteria or other undesirable substances to accumulate on the components. Accordingly, it is presently recognized that it may be desirable to clean the components.

BRIEF DESCRIPTION

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

In one embodiment, a method of operating a cleaning and transferring system in a venue with a first location and a second location includes receiving one or more accessories onto a conveyor at the second location. The method also includes transferring the one or more accessories from the second location to the first location via the conveyor. The method further includes cleaning the one or more accessories during the transferring of the one or more accessories from the second location to the first location via the conveyor. The method further includes receiving one or more guest items onto the conveyor at the first location. The method further includes transferring the one or more guest items from the first location to the second via the conveyor.

In one embodiment, a device cleaning and transferring system for use in a venue that has a first location and a second location includes a conveyor formed in a continuous loop, a second access zone that enables guests to deposit one or more accessories onto the conveyor at the second location, and a first access zone that enables the guests to retrieve the one or more accessories from the conveyor at the first location. The device cleaning and transferring system also includes a cleaning device positioned along the conveyor between the second access zone and the first access zone to clean the one or more accessories as the one or more accessories are transferred from the second access zone to the first access zone via the conveyor.

In one embodiment, an environment includes an entrance portion, an attraction portion, and an exit portion. The environment also include a device cleaning and transferring system with a conveyor configured to transfer one or more guest items from a first location between the entrance portion and the attraction portion to a second location between the attraction portion and the exit portion, as well as a guest item cleaning device positioned along the conveyor to clean the one or more guest items as the one or more guest items are transferred from the first location to the second location via the conveyor.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
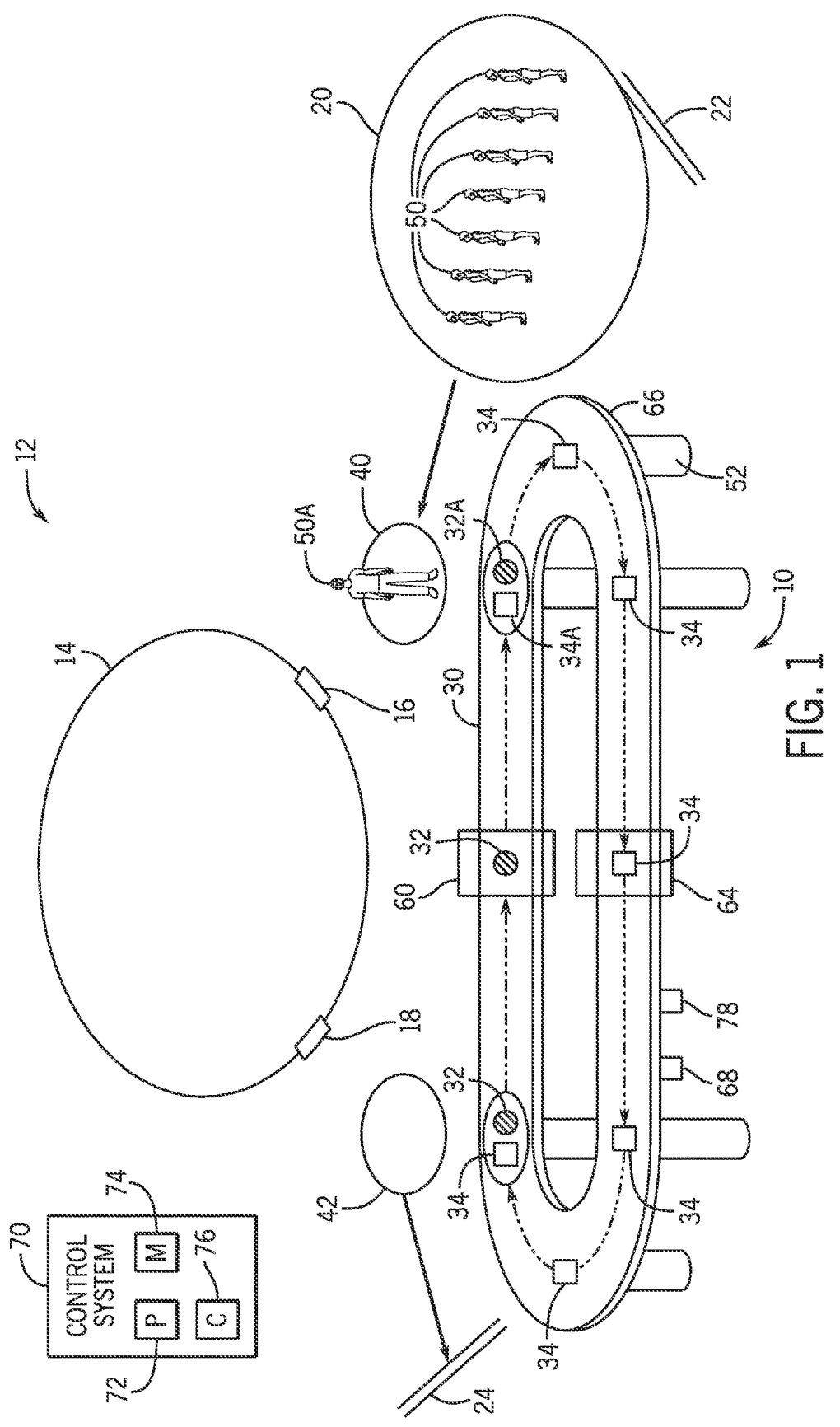
FIG. 1 is a schematic diagram of a cleaning and transferring system in an environment at a first time, in accordance with an embodiment of the present disclosure.

One or more or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The present embodiments disclosed herein relate to device cleaning and transferring systems and methods. The device cleaning and transferring systems and methods may be utilized in any of a variety of environments, such as entertainment environments. For example, the device cleaning and transferring systems and methods may be utilized to clean (e.g., wash, disinfect, sanitize) and/or transfer items (e.g., accessories and/or guest items) in amusement parks, theatres, restaurants, and so forth. It should be appreciated that the device cleaning and transferring systems and methods may be utilized to clean and/or transfer items in airports, airplanes, hotels, and/or any other environment or venue with an entry and an exit. Further, it should be appreciated that the device cleaning and transferring systems and methods may be utilized to clean and/or transfer items in any other environment or venue where the items are contacted by and/or exposed to guests and/or other personnel (e.g., employees) and/or other sources of bacteria, undesirable particles, and so forth.

Advantageously, the cleaning and transferring systems and methods disclosed herein provide efficient cleaning and/or transfer of items. For example, a guest may pass through an entrance to visit an attraction, such as a ride attraction in an amusement park. As the guest travels through a queue toward a ride vehicle, the guest may reach a first location where the guest has access to (e.g., can pick up or obtain) an accessory via a cleaning and transferring system associated with the ride attraction. The accessory may be a virtual reality (VR) and/or augmented reality (AR) headset, a handheld blaster that enables the guest to launch virtual projectiles, and/or any other item configured to be carried (e.g., worn and/or held) by the guest in the ride attraction. At the first location, the guest may also deposit a guest item at the cleaning and transferring system. Then, the guest (with the accessory) may load into the ride vehicle and travel through the ride attraction for a ride experience. At a conclusion of the ride experience, the guest (with the accessory) may unload from the ride vehicle and reach a second location on their way to an exit of the ride attraction. At the second location, the guest may have access to (e.g., can pick up or retrieve) the guest item and may also deposit the accessory at the cleaning and transferring system. Then, the guest may leave the ride attraction with the guest item, and the accessory may be returned to the first location via the cleaning and transferring system.

To achieve efficient cleaning and transferring of the accessory (e.g., which may be used by multiple guests over time; for pick up by another guest at the first location), the cleaning and transferring system may clean the accessory as a conveyor moves the accessory from the second location to the first location. For example, the cleaning and transferring system may carry the accessory through a cleaning zone that includes one or more cleaning devices that apply heat, ultraviolet light, soap and water, and/or any other cleaning and/or sanitizing technique(s). To simultaneously achieve efficient transferring of the guest item (e.g., which may be owned by the guest and may be carried by the guest into and out of the ride attraction), the cleaning and transferring system may carry the guest item with the conveyor from the first location to the second location as the guest enjoys the ride experience. The cleaning and transferring system may also clean the guest item, such as by carrying the guest item through an additional cleaning zone that includes one or more additional cleaning devices. Further, in some embodiments, the cleaning and transferring system may charge the accessory and/or the guest item.

FIG. 1 is a schematic diagram of an embodiment of a cleaning and transferring system 10 (also referred to herein as "the system 10") that may be utilized in an environment 12. It should be appreciated that the environment 12 may include any of a variety of features and/or may be used for any of a variety of purposes. For example, the environment 12 may include or be an attraction, such as a ride attraction with a ride vehicle, a walk-through attraction that is traversed via walking along stationary and/or movable paths (e.g., conveyors), a show attraction that includes visible and/or audible entertainment, a game attraction that includes collecting points and/or other achievements, an interactive attraction that includes interacting with real and/or virtual actors, and so forth.

To facilitate discussion, in FIG. 1, the environment 12 is an attraction in an amusement park and includes an attraction portion 14 with a loading zone 16 and an unloading zone 18, as well as a queue portion 20, an entrance portion 22, and an exit portion 24. For example, guests 50 may visit and experience the environment 12 by passing through the entrance portion 22, waiting in the queue portion 20 for some period of time, then using the loading zone 16 to load onto a ride vehicle or to otherwise pass into the attraction portion 14, then using the unloading zone 18 to unload from the ride vehicle or to otherwise pass out of the attraction portion 14, and then exiting out of the exit portion 24.

The system 10 is utilized in and/or integrated with the environment 12 to clean and/or transfer items for the guests 50. As shown, the system 10 includes a conveyor 30 (e.g., conveyor system) that is configured to support the items, which may include one or more accessories 32 and/or one or more guest items 34. The conveyor 30 may be a belt conveyor that supports the items on top of the belt conveyor, the conveyor 30 may be rollers that are driven to rotate to roll the items over the top of the rollers, or the conveyor 30 may be a track that suspends the items on hangers below the track. The conveyor 30 may be a single, continuous loop that carries both the one or more accessories 32 and/or the one or more guest items 34. However, the conveyor 30 may include multiple loops and/or levels (e.g., the belt conveyor for one type of the items, such as the one or more guest items 34, and the track positioned vertically above the belt conveyor and for another type of the items, such as the one or more accessories 32). Further, the conveyor 30 may include physically separate conveyor portions, such as a first conveyor portion that carries any items thereon in a first direction (e.g., the one or more accessories 32 in the first direction) and a second conveyor portion that carries any items thereon in a second direction (e.g., the one or more guest items 34 in the second direction). In some cases, the first direction may be opposite the second direction. In some cases, the first conveyor portion and the second conveyor portion may be stacked vertically (e.g., one above the other) and/or laterally (e.g., side-by-side). Thus, the conveyor 30 may include the physically separate conveyor portions that operate as separate one-way conveyors (e.g., not a continuous loop; do not carry the items in a continuous loop; separate conveyors that may be considered part of a conveyor system). Indeed, the conveyor 30 may include any number of conveying structures (e.g., multiple belts and/or tracks) and may generally have any suitable form that facilitates transfer of the items, as described herein. The conveyor 30 may be supported on a frame 52, such as a frame mounted to a floor or to a ceiling of a structure. In one embodiment, the conveyor 30 may be separate from the attraction portion 14 (e.g., outside of the attraction portion 14) or at least separate from ride vehicles or other structures that the guests 50 view and/or interact with while the guests 50 are in the attraction portion 14.

The one or more accessories 32 may include shared portable devices that are configured to be carried (e.g., held and/or worn) by the guests 50. For example, the one or more accessories 32 may include VR and/or AR headsets, handheld blasters or other targeting devices that enable the guests 50 to launch virtual projectiles, wands, toys, figurines, clothing, jewelry, wristbands, headgear, medallions, glasses (e.g., corrective lens glasses, sunglasses, three-dimension

[3D] glasses), and/or any combination thereof. Each of the one or more accessories 32 may be configured to be used by multiple different guests 50 over time. The one or more guest items 34 may include personal portable devices that are configured to be carried (e.g., held and/or worn) by the guests 50. For example, the one or more guest items 34 may include mobile phones, tablets, watches, cameras, laptop computers, e-readers, toys, clothing, bags, glasses, food items, and/or any combination thereof. Each of the one or more guest items 34 may be owned by and/or associated with (e.g., permanently associated with) a respective guest 50. Thus, as described in more detail herein, each of the one or more accessories 32 may be cleaned and/or transferred by the system 10 to enable each of the one or more accessories 32 to be used by the multiple different guests 50 in the attraction portion 14 over time, while each of the one or more guest items 34 may be cleaned and/or transferred by the system 10 to enable the respective guest 50 to enjoy the attraction portion 14 without carrying the guest item 34 in the attraction portion 14.

As shown in FIG. 1, the environment 12 includes a first location 40 (e.g., zone, region, area) traversed or visited by the guests 50, such as while the guests 50 travel from the entrance portion 22 to the attraction portion 14. For example, the first location 40 may be located at or near an end of the queue portion 20 and/or adjacent to the loading zone 16. Further, the environment 12 includes a second location 42 (e.g., zone, region, area) traversed or visited by the guests 50, such as while the guests 50 travel from the attraction portion 14 to the exit portion 24. For example, the second location 42 may be located adjacent to the unloading zone 18. In any case, the system 10 includes the conveyor 30 that travels through or past the first location 40 and the second location 42. Thus, when the guests 50 are at the first location 40 and the second location 42, the guests 50 may access the conveyor 30 (e.g., access zones; items, such as the one or more accessories 32 and the one or more guest items 34, on the conveyor 30). In one embodiment, the guests 50 may retrieve and deposit the one or more accessories 32 and/or the one or more guest items 34 during movement via the conveyor 30. However, it should be appreciated that other features are envisioned. For example, the one or more accessories 32 may be transferred into one or more accessory bins at the first location 40 (e.g., via configuration of the conveyor 30; via robotic arms (e.g., mechanical arms, electromagnetic arms, soft robotic arms, arms comprising pneumatic suction) and/or the one or more guest items 34 may be transferred into one or more guest item bins at the second location 42 (e.g., via configuration of the conveyor 30; via robotic arms) to facilitate access to the guests 50. It should be appreciated that the first location 40 and the second location 42 are described herein with reference to certain other portions of the environment to facilitate discussion; however, the first location 40 may be at any suitable portion of the environment 12, such as between the entrance portion 22 and the loading zone 16 of the attraction portion 14, at the entrance portion 22, and/or at the loading zone 16 of the attraction portion 14. Similarly, the second location 42 may be at any suitable portion of the environment 12, such as between the exit portion 24 and the unloading zone 18 of the attraction portion 14, at the exit portion 24, and/or at the unloading zone 18 of the attraction portion 14.

Figure 2:
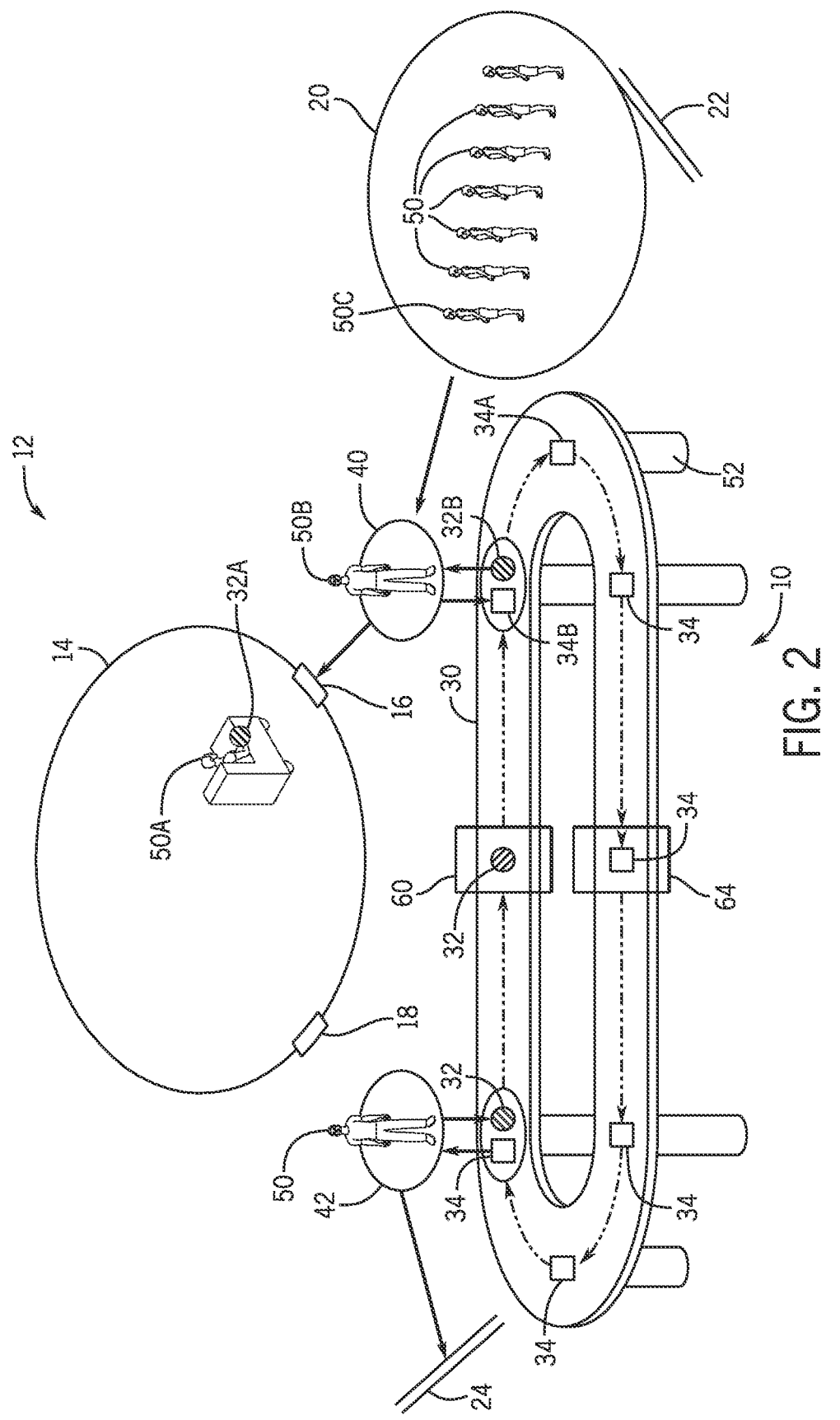
FIG. 2 illustrates the cleaning and transferring system of FIG. 1 at a second time, in accordance with an embodiment of the present disclosure.
Figure 3:
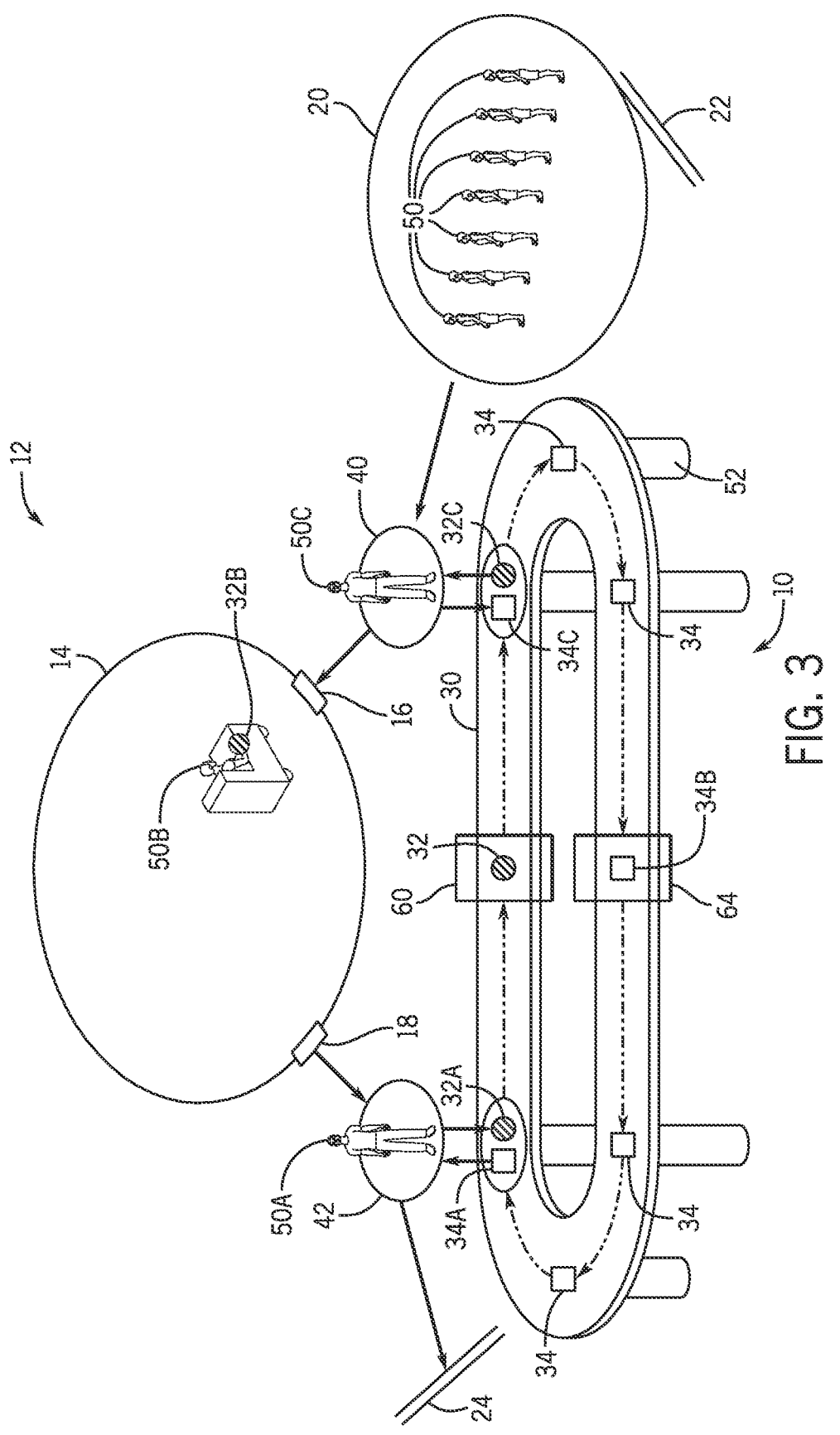
FIG. 3 illustrates the cleaning and transferring system of FIG. 1 at a third time, in accordance with an embodiment of the present disclosure.

Operational features of the system 10 may be understood with reference to FIGS. 1-3. In particular, FIG. 1 is a schematic diagram of the system 10 and the environment 12 at a first time with a first guest 50A in the first location 40. FIG. 2 is a schematic diagram of the system 10 and the environment 12 at a second time with the first guest 50A in the attraction portion 14 and a second guest 50B in the first location 40. FIG. 3 is a schematic diagram of the system 10 and the environment at a third time with the first guest 50A in the second location 42, the second guest 50B in the attraction portion 14, and a third guest 50C in the first location 40.

As shown, in FIG. 1, the first guest 50A is in the first location 40 and has access to a portion of the conveyor 30 (e.g., first access zone). In particular, the first guest 50A may be able to pick up a first accessory 32A of the one or more accessories 32 from the conveyor 30 and/or deposit a first guest item 34A of the one or more guest items 34 onto the conveyor 30. Then, the first guest 50A may carry the first accessory 32A to the loading zone 16 and into the attraction portion 14.

For example, as shown in FIG. 2, the first guest 50A may carry the first accessory 32A onto a ride vehicle that travels through the attraction portion 14 (e.g., along a path). As the first guest 50A moves through the attraction portion 14, the first guest item 34A may be carried (e.g., transferred) from the first location 40 toward the second location 42 via the conveyor 30. Additionally, the second guest 50B may reach the first location 40 and may have access to a portion of the conveyor 30 (e.g., first access zone). In particular, the second guest 50B may be able to pick up a second accessory 32B of the one or more accessories 32 from the conveyor 30 and/or deposit a second guest item 34B of the one or more guest items 34 onto the conveyor 30. Then, the second guest 50B may carry the second accessory 32B to the loading zone 16 and into the attraction portion 14.

With reference to FIG. 3, the first guest 50A may complete the ride experience and then reach the unloading zone 18. The first guest 50A may carry the first accessory 32A off of the ride vehicle, through the unloading zone 18, and to the second location 42. The first guest 50A may deposit the first accessory 32A onto the conveyor 30 (e.g., at a second access zone). Further, the conveyor 30 may present the first guest item 34A or make the first guest item 34A accessible to the first guest 50A while the first guest 50A is at the second location 42 (e.g., at the second access zone). For example, the conveyor 30 may have particular parameters (e.g., speed, length) and/or move according to timing control signals that cause the first guest item 34A to reach the second location 42 as the first guest 50A reaches the second location 42 (e.g., enters the second location 42 and/or is positioned within the second location 42). In this way, the first guest 50A may efficiently return the first accessory 32A and retrieve the first guest item 34A as they travel toward the exit portion 24 of the environment 12. The conveyor 30 may then return the first accessory 32A to the first location 40, and the conveyor 30 may direct and/or carry the first accessory 32A through a cleaning device 60 that cleans the first accessory 32A during transfer of the first accessory 32A to the first location 40.

Further, as shown in FIG. 3, the second guest 50B may carry the second accessory 32B onto another ride vehicle (or the ride vehicle) that travels through the attraction portion 14. As the second guest 50B moves through the attraction portion 14, the second guest item 34B may be carried (e.g., transferred) from the first location 40 toward the second location 42 via the conveyor 30. Additionally, the third guest 50C may reach the first location 40 and may have access to a portion of the conveyor 30 (e.g., first access zone). In particular, the third guest 50C may be able to pick up a third accessory 32C of the one or more accessories 32 from the conveyor 30 and/or deposit a third guest item 34C of the one or more guest items 34 onto the conveyor 30. Then, the third guest 50C may carry the third accessory 32C to the loading zone 16 and into the attraction portion 14. In this way, the guests 50 may efficiently obtain and return the one or more accessories 32 to facilitate use of the one or more accessories 32 by multiple guests 50 in the attraction portion 14 over time, and the guests 50 may also deposit the one or more guest items 34 to be carried by the system 10 as the guests 50 experience the attraction portion 14.

As shown in FIGS. 1-3, the cleaning device 60 may be positioned along the conveyor 30 to clean the one or more accessories 32 as the one or more accessories 32 are conveyed (e.g., transferred) from the second location 42 to the first location 40. Thus, after each use by one of the guests 50, the one or more accessories 32 pass through the cleaning device 60 to be cleaned prior to being accessed by other guests 50 at the first location 40. The cleaning device 60 may be configured to clean (e.g., sanitize) the one or more accessories 32 via heat, ultraviolet light, soap and water, other cleaning fluid, and/or any other suitable cleaning technique. Further, it should be appreciated that multiple cleaning devices 60 (e.g., 2, 3, 4, 5, or more) may be positioned along the conveyor 30 to clean the one or more accessories 32 as the one or more accessories 32 are conveyed (e.g., transferred) from the second location 42 to the first location 40. In such cases, each of the one or more accessories 32 may go through a multi-stage cleaning process, such as a fluid wash treatment, a first drying heat treatment, a second heat treatment, and/or an ultraviolet light treatment, and so forth.

The system 10 is configured to coordinate with the attraction portion 14. For example, the system 10 is configured to coordinate with the attraction portion 14 to synchronize presentation of the one or more guest items 34 at the second location 42 with arrival of the guests 50 at the second location 42. In one embodiment, during normal operations, the conveyor 30 may move continuously at a constant speed. Thus, the conveyor 30 may generally move continuously at the constant speed to enable a line of the guests 50 to travel from the queue portion 20, through the first location 40 to pick up a respective one of the one or more accessories 32 and/or to drop off a respective one of the one or more guest items 34, through the attraction portion 14, and then through the second location 42 to pick up the respective one of the one or more guest items 34 and/or to drop of the respective one of the one or more accessories 32. In such cases, the constant speed may be selected such that a time of travel of the respective one of the one or more guest items 34 from the first location 40 to the second location 42 corresponds (e.g., matches) a time (e.g., an expected travel time; an average travel time; based on known timing signals, empirical data, and/or modeled data; one ride cycle) that it takes the guests 50 to travel from the first location 40 to the second location 42 via the attraction portion 14.

In one embodiment, the conveyor 30 may be dynamically controlled based on one or more inputs. The one or more inputs may be indicative of the time that it takes the guests 50 to travel from the first location 40 to the second location 42 via the attraction portion 14, as the time may change based on various factors. For example, the conveyor 30 may be controlled to move slower (e.g., relative to the constant speed during the normal operations) in response to the one or more inputs that indicate a delay in the attraction portion 14. More particularly, the conveyor 30 may be controlled to move slower (e.g., non-zero speed and/or stopped) in response to the one or more inputs that indicate that the ride vehicle is temporarily stopped within the attraction portion 14, such as due to maintenance needs, loading issues, unloading issues, and so forth. In this way, the conveyor 30 may be controlled to provide the one or more guest items 34 to the guest(s) 50 in the ride vehicle that was temporarily stopped within the attraction portion 14 as the guest(s) 50 reach the second location 42 (e.g., to account for the delay in the attraction portion 14, and a corresponding delay in arrival/travel time of the guests). Indeed, the conveyor 30 may be dynamically controlled based on current parameters (e.g., speed, timing, duration) of operation of the attraction portion 14 to thereby present the one or more guest items 34 to the guests 50 as the guests 50 reach the second location 42 (e.g., present a respective one of the one or more guest items 34 to a particular guest 50 that deposited the respective one of the one or more guest items 34 as the particular guest 50 reaches the second location 42).

In one embodiment, during normal operations, the conveyor 30 may move in increments that correspond to ride vehicle groups. For example, the conveyor 30 may move over a first time period at a constant speed to allow a first group of guests 50 at the second location 42 to deposit respective accessories 32 onto the conveyor 30 and to pick up respective guest items 34 from the conveyor 30, and also to simultaneously allow a second group of guests 50 at the first location 40 to pick up respective accessories 32 from the conveyor 30 and to deposit respective guest items 34 onto the conveyor 30. Then, the conveyor 30 may move through some distance to align the accessories 32 used by the first group of guests 50 with the cleaning device(s) 60. Then, the conveyor 30 may pause to enable thorough cleaning of the accessories 32 used by the first group of guests 50 with the cleaning device(s) 60. Then, the conveyor 30 may resume movement at the constant speed to allow the second group of guests 50 at the second location 42 to deposit respective accessories 32 onto the conveyor 30 and to pick up respective guest items from the conveyor 30, and also to simultaneously allow a third group of guests 50 at the first location 40 to pick up respective accessories 32 (which may be the same accessories used by the first group of guests 50) from the conveyor 30 and to deposit respective guest items 34 onto the conveyor 30. As described in more detail herein, the system 10 may utilize unique identifiers to facilitate coordination and synchronization of the conveyor 30 with the attraction portion 14 (e.g., to present the one or more guest items 34 at appropriate times).

In one embodiment, the system 10 may include an additional cleaning device 64 positioned along the conveyor 30 to clean the one or more guest items 34 as the one or more guest items 34 are conveyed (e.g., transferred) from the first location 40 to the second location 42. Thus, the one or more guest items 34 pass through the additional cleaning device 64 to be cleaned prior to being retrieved by the guests 50 at the second location 42. The additional cleaning device 64 may be configured to clean (e.g., sanitize) the one or more guest items 34 via heat, ultraviolet light, soap and water, other cleaning fluid, and/or any other suitable cleaning technique. Further, it should be appreciated that multiple additional cleaning devices 64 (e.g., 2, 3, 4, 5, or more) may be positioned along the conveyor 30 to clean the one or more guest items 34 as the one or more guest items 34 are conveyed (e.g., transferred) from the first location 40 to the second location 42. In such cases, each of the one or more guest items 34 may go through a multi-stage cleaning process, such as a first drying heat treatment, a second heat treatment, and/or an ultraviolet light treatment, and so forth. In one embodiment, the cleaning device 60 may extend across the conveyor 30 to operate as the additional cleaning device 64 (e.g., to clean the one or more accessories 32 that travel from the second location 42 to the first location 40, as well as to clean the one or more guest items 34 that travel from the first location 40 to the second location 42).

As described in more detail herein, in one embodiment, the guests 50 may be able to opt in and/or to opt out of the cleaning process for the one or more guest items 34. For example, one or more input devices (e.g., switches, buttons, readers, scanners) located on the conveyor 30, at the first location 40, and/or at some other suitable location may enable and/or receive one or more cleaning inputs that indicate whether the guests 50 opt in and/or opt out of the cleaning process for the one or more guest items 34. Indeed, the one or more cleaning inputs may indicate particular parameters (e.g., type, temperature) of the cleaning process for the one or more guest items 34. As noted herein, the system 10 may be devoid of any cleaning device along a portion of the conveyor 30 that carries the one or more guest items 34 from the first location 40 to the second location 42. Thus, the system 10 may be designed not to clean (e.g., via any techniques, such as heat, ultraviolet light, fluid) the one or more guest items 34. That is, the system 10 may only have the cleaning device 60 along a portion of the conveyor 30 that carries the one or more accessories 32 from the second location 42 to the first location 40. Thus, the system 10 may be designed to only clean the one or more accessories 32 and not to clean the one or more guest items 34.

In one embodiment, the system 10 may be configured to charge the one or more accessories 32 as the one or more accessories 32 are transferred via the conveyor 30. Additionally or alternatively, the system 10 may be configured to charge the one or more guest items 34 as the one or more guest items 34 are transferred via the conveyor 30. For example, a bus bar 66 that is coupled to a current source 68 is shown in FIG. 1 to facilitate discussion. The bus bar 66 may be configured to contact conductors and/or contacts of the one or more accessories 32 and/or the one or more guest items 34 on the conveyor 30. The bus bar 66 may be configured to contact conductors and/or contacts of one or more cables (e.g., USB, USB-C, Lighting, Micro USB) that extend to (e.g., connect or plug into) the one or more accessories 32 and/or the one or more guest items 34 on the conveyor 30. Thus, a flow of current from the current source 68 through the bus bar 66 enables the bus bar 66 to charge power storage components of the one or more accessories 32 and/or the one or more guest items 34 on the conveyor 30. In this way, the bus bar 66 and associated components (e.g., the conductors, the contacts, and/or the one or more cables) provide wired charging to the one or more accessories 32 and/or the one or more guest items 34 on the conveyor 30. The bus bar 66 may extend along an entire length of the conveyor 30 (e.g., about the continuous loop) or some portion of the entire length of the conveyor 30. Further, it should be appreciated that any of a variety of techniques may be utilized to charge the one or more accessories 32 as the one or more accessories 32 are transferred via the conveyor 30. For example, the system 10 may implement wireless charging techniques via inductive charging, magnetic resonance, radio-frequency power harvesting, and so forth. In one embodiment, the guests 50 may be able to opt in and/or to opt out of the charging process for the one or more guest items 34.

To facilitate the disclosed techniques, the system 10 may include or be associated with a control system 70 (e.g., electronic control system (e.g. controller)), which is shown in FIG. 1 to facilitate discussion. The control system 70 includes a processor 72, a memory device 74, and a communication system 76 (e.g., one or more communication devices, communication circuitry), wherein the communication system may include wired communication systems and/or wireless communication systems (e.g., including transmitters, receivers, and/or transceivers). The processor 72 may include one or more processors and may be any type of computer processor or microprocessor capable of executing computer-executable code. The memory device 74 may include one or more memory devices and may be any suitable article of manufacture that can serve as media to store processor-executable code, data, or the like. The article of manufacture may represent computer-readable media (e.g., any suitable form of memory or storage) that may store the processor-executable code used by the processor 72 to perform various techniques disclosed herein. The memory device 74 may represent non-transitory computer-readable media (e.g., any suitable form of memory or storage). It should be noted that non-transitory merely indicates that the media is tangible and not a signal.

It should be noted that the components described above with regard to the control system 70 are merely examples, and the control system 70 may include additional or fewer components. In some embodiments, the control system 70 may be a distributed control system that includes multiple processors (e.g., including one or more cloud computing systems having multiple processors). Indeed, as used herein, the term "control system" refers to an electronic control system or computing system such as, but not limited to, a single computer, virtual machine, virtual container, host, server, laptop, and/or mobile device, or to multiple electronic computing devices working together to perform the function described as being performed on or by the controller. The communication system 76 may include one or more communication devices and may be any suitable device that is configured to communicate with other devices and systems (e.g., the cleaning device 60, the additional cleaning device 64, the current source 68 and/or other charging devices, a drive system 78 for the conveyor 30, input devices, sensors, and/or an attraction control system) via a network.

Figure 4:
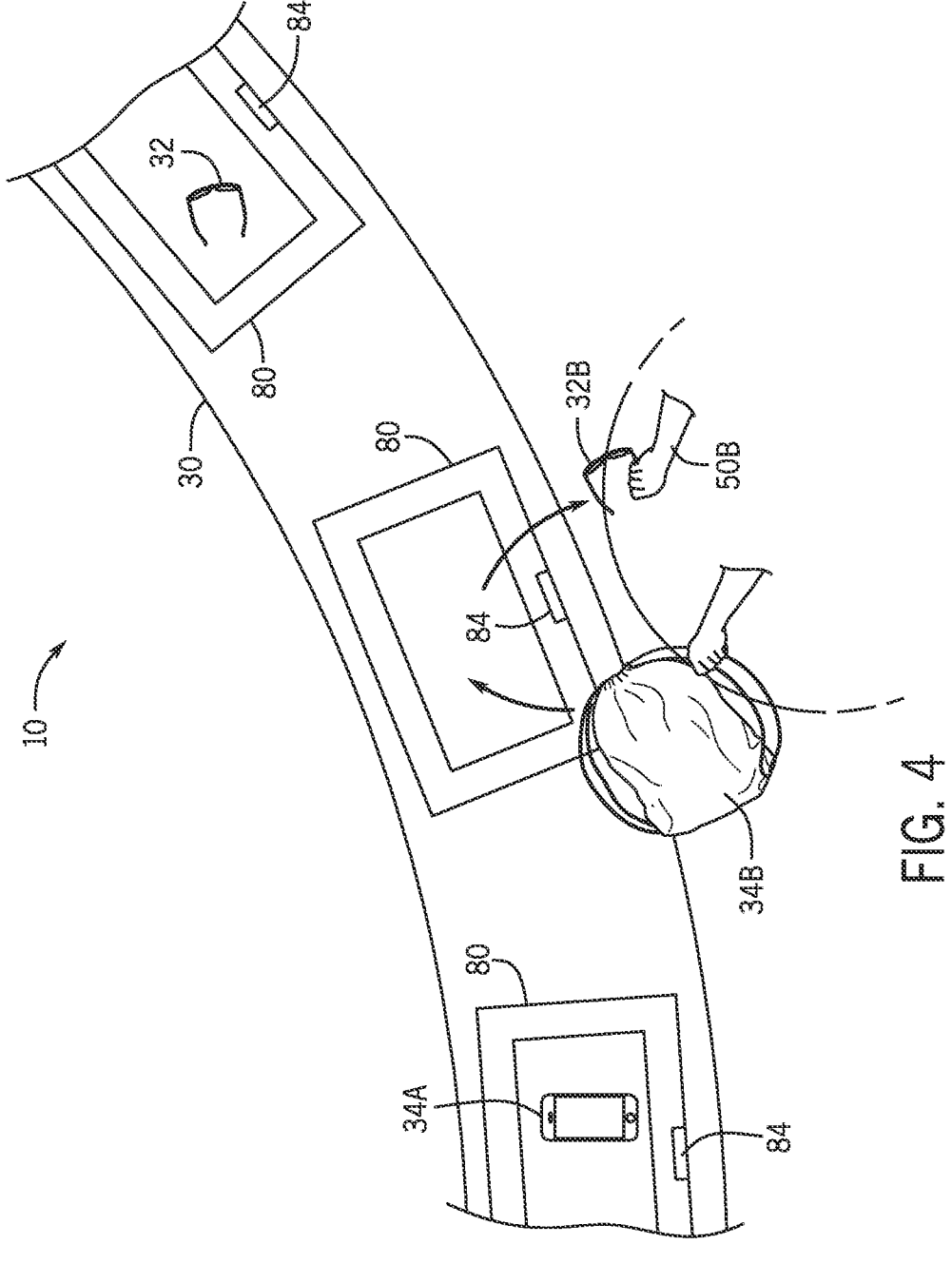
FIG. 4 illustrates a portion of the cleaning and transferring system of FIG. 1, wherein the cleaning and transferring system includes containers to hold accessories, guest items, or both, in accordance with an embodiment of the present disclosure.

FIG. 4 is an embodiment of a portion of the system 10 with containers 80 to hold accessories, guest items, or both. In one embodiment, the containers 80 may be integrally formed and/or fixed to the conveyor 30. In one embodiment, the containers 80 may be separate from the conveyor 30 and may be movable relative to the conveyor 30. For example, at the first location, the containers 80 may be picked up by the guests to allow the guests to obtain the one or more accessories 32 from the containers 80 and to place the one or more guest items 34 into the containers 80. Then, the guests may place the containers 80 back onto the conveyor 30, and the containers 80 may lock into place on (e.g., couple to) the conveyor 30 (e.g., key fit; magnet system) and/or may roll along the conveyor 30 (e.g., via the rollers of the conveyor 30 and/or passive or driven wheels on the containers 80).

In one embodiment, the containers 80 may lock into place on the conveyor 30 via a magnet system that includes one or more electromagnets integrated into the conveyor 30, the containers 80, or both. The one or more electromagnets may be configured to selectively engage with (e.g., magnetically couple to) a corresponding reaction material that is integrated into the conveyor 30, the containers 80, or both. The corresponding reaction material may include one or more strips of metallic material (e.g., ferromagnetic material, such as iron), permanent magnets, other electromagnets, and/or any other suitable magnetically attractable material. As an example, in one embodiment, the one or more electromagnets may be integrated with the conveyor 30 and the corresponding reaction material may be integrated with the containers 80. As such, the one or more electromagnets may be selectively energized, de-energized, or a have a magnetic polarity reversed to facilitate transitioning the conveyor 30 and the containers 80 between an engaged configuration in which the one or more electromagnets attract the corresponding reaction material, and a detached configuration (e.g., a decoupled or disengaged configuration) in which the one or more electromagnets do not attract the corresponding reaction material and/or repel the corresponding reaction material. Moreover, a current supplied to each of the one or more electromagnets may be independently adjustable (e.g., via the control system 70) to modulate a magnetic coupling force between the one or more electromagnets and the corresponding reaction material and, thus, transiently adjust a coupling strength between the conveyor 30 and the containers 80.

In one embodiment, the containers 80 may lock into place on the conveyor 30 via the magnet system that includes one or more permanent magnets integrated into the conveyor 30, the containers 80, or both. The one or more permanent magnets may be configured to engage with (e.g., magnetically couple to) a corresponding reaction material that is integrated into the conveyor 30, the containers 80, or both. It should be appreciated that the magnet system may include any of a variety of features and components that enable the conveyor 30 to magnetically couple to the containers 80.

The containers 80 may facilitate other operations, such as proper placement of the one or more accessories 32 and/or the one or more guest items 34 on the conveyor 30 for transferring, cleaning, and/or charging, for example. In one embodiment, the containers 80 may include cables, contacts, and/or charging pads 82 that facilitate wired and/or wireless charging of the one or more accessories 32 and/or the one or more guest items 34 placed onto the contacts and/or charging pads 82.

In one embodiment, the containers 80 may include input devices 84, such as switches, buttons, readers, and/or scanners. The input devices 84 may enable and/or receive one or more inputs, such as the one or more cleaning inputs that indicate whether the guests opt in and/or opt out of the cleaning process for the one or more guest items 34. For example, the input devices 84 may include switches that the guests can switch between an "on" position and an "off" position to opt in or to opt out, respectively, of the cleaning process. More particularly, a particular guest may place a respective one of the one or more guest items 34 into a respective one of the containers 80, and then adjust the switch to the "on" position to select the cleaning process. Then, the position of the switch in the "on" position may be read by and/or communicated to the additional cleaning device to cause the additional cleaning device to carry out the cleaning process for the respective one of the one or more guest items 34 in the respective one of the containers 80. However, is the particular guest had adjusted the switch to the "off" position to opt out of the cleaning process, then the additional cleaning device would not carry out the cleaning process for the respective one of the one or more guest items 34 in the respective one of the containers 80. It should be appreciated that the input devices 84 may include multiple buttons (e.g., physical buttons or virtual displayed buttons) that the guests can actuate to opt in or to opt out of the cleaning process and/or to make more specific selections (e.g., a type of the cleaning process).

In one embodiment, the input devices 84 may include readers (e.g., radiofrequency identification readers) or scanners (e.g., quick response code scanners) that are configured to receive unique identifiers (e.g., from radiofrequency tags or quick response codes). Then, once the unique identifiers are obtained via the input devices 84, the unique identifiers may be utilized to reference a database (e.g., in the memory device of the control system or otherwise accessible to the control system). For example, the database may include a lookup table that correlates each unique identifier to one or more preferences for the cleaning process. In such cases, a particular guest may indicate a respective preference via an application (e.g., software application), and the respective preference is then linked to a particular unique identifier for the particular guest. Then, the particular guest may tap a device (e.g., one of the one or more guest devices 34; a wearable; a mobile device) at a particular input device 84 for one of the containers 80 (e.g., bring into proximity; within a communication range of the particular input device 84). Then, the particular input device 84 may communicate the particular unique identifier for the particular guest to the control system, which may then control and operate the additional cleaning device (and/or the system 10, generally) based on the respective preference of the particular guest.

It should be appreciated that similar operational features may be provided for charging processes. For example, the input devices 84 may also enable and/or receive one or more inputs, such as the one or more charging inputs that indicate whether the guests opt in and/or opt out of the charging process for the one or more guest items 34. In this way, the guests may provide the one or more inputs to control treatment of the one or more guest items 34 as the one or more guest items 34 are handled by the system 10. For example, certain guests may not want any cleaning process on any of their respective guest items 34, while other guests may want all cleaning processes on all of their respective guest items 34, and yet other others may want only certain cleaning processes on only some of their respective guest items 34, and so forth. For example, the first guest item 34A may be only a mobile phone, and the first guest may provide a respective input to select the cleaning process with only ultraviolet light. However, the second guest 50B may deposit the second guest item 34B that include a purse with many different items inside the purse, and the second guest 50B may provide a respective input to opt out of the cleaning process.

In this way, each guest may provide their own respective inputs and make their own selections each time they provide their respective guest items 34 to the system 10, each guest may provide default inputs or preferences that apply to multiple systems 10 (e.g., at different attractions or environments of an amusement park), and so forth. Advantageously, the guests can elect to have their respective guest items 34 cleaned each time they visit the environment 12, as well as to have their respective guest items 34 held and transferred each time they visit the environment 12 (and/or other environments, including different attractions or environments of an amusement park). Furthermore, the one or more guest items 34 may be held and transferred with appropriate timing control to coincide with arrival of particular guests at the second location, and may also be held and transferred via the conveyor 30 that also transfers the one or more accessories 32.

The unique identifiers may facilitate return of the one or more guest items 34 via the conveyor 30. For example, each container 80 may be associated with (e.g., temporarily, such as during one ride cycle) a particular ride vehicle of the attraction portion (e.g., based on a position of the particular ride vehicle relative to the loading zone when a particular guest places their respective guest items in the container 80). This enables the system 10 to adjust and synchronize delivery of the one or more items 34 to the second location even if the particular ride vehicle passes other ride vehicles or otherwise moves to the unloading zone out of order relative to the other ride vehicles. To accommodate these aspects, the conveyor 30 may be configured to adjust and change an order in which the one or more guest items 34 are presented at the second location 42. For example, the conveyor 30 may have multiple branches that deliver to respective bays (e.g., exit bays), as well as mechanical arms or guides that transfer appropriate ones of the one or more guest items 34. As another example, the conveyor 30 may remove the one or more guest items 34 from the conveyor 30, and then replace the one or more guest items 34 onto the conveyor 30 in the order and with timing that causes the one or more guest items 34 to reach the second location in a synchronized manner with arrival of the guests.

Further, in one embodiment, each of the one or more accessories 32 may have a unique identifier that enables each of the one or more accessories 32 to act as a key to unlock access to corresponding guest items of the one or more guest items 34 at the second location 42. For example, with reference to FIG. 4, the unique identifier of the second accessory 32B may be read by the particular input device 84 of the particular container 80 and is then associated with the particular container 80. The second guest 50B may also place the second guest item 34B into the particular container 80. The second guest 50B may then move through the attraction portion and then later pick up the second guest item 34B at the second location by presenting the second accessory 32B to be read by the particular input device 84 of the particular container 80. For example, the particular container 80 may have a door or a lid that is configured to unlock and/or open in response to the second accessory 32B being read by the particular input device 84 of the particular container 80 in this way. The unique identifier on the second accessor 32B may also facilitate tracking the location of the second guest 50B (e.g., through the attraction portion) for synchronized delivery of the second guest item 34B to the second location (e.g., available upon arrival of the second guest 50B at the second location). It should be appreciated that these techniques may be implemented without any containers, but instead with sections or pads on the conveyor 30. Further, as noted herein, the conveyor 30 may have multiple branches that deliver to respective bays (e.g., exit bays), as well as mechanical arms or guides that transfer appropriate ones of the one or more guest items 34 to facilitate the synchronized delivery and/or provide additional time for unlocking processes. It should be appreciated that the conveyor 30 may have multiple branches that receive items, such as the one or more guest items 34 from multiple different starting points, such as in cases in which the guests enter or access the first location 40 via one or more priority lines, one or more single rider lines, one or more virtual queue lines, and so forth. It should be appreciated that the containers 80 may include any of a variety of lock configuration, including mechanical locks, electromagnetic locks, and so forth. Further, each container 80 may be assigned to a group of guests who experience the attraction together (e.g., in a single ride vehicle; one group that walks together along a stationary and/or moving path) via one or more unique identifiers associated with the group of guests.

It should also be appreciated that any of a variety of types of unique identifiers, including biometric data, may be utilized to provide access to each container 80. For example, the biometric data (e.g., voice recognition, facial recognition, finger print) of the second guest 50B may be read by the particular input device 84 of the particular container 80 as the second guest 50B places the second guest item 34B in the particular container 80. Then, the second guest 50B may later pick up the second guest item 34B at the second location by allowing the biometric data to be read by the particular input device 84 of the particular container 80.

Similarly, each guest may retain a retained guest item (e.g., mobile device, wearable, and/or card; brought in by each guest and/or provided to each guest that wishes to use the system 10) that includes a respective unique identifier, such as a quick response code or a bar code. For example, the respective unique identifier of the retained guest item of the second guest 50B may be read by the particular input device 84 of the particular container 80 as the second guest 50B places the second guest item 34B in the particular container 80. Then, the second guest 50B may later pick up the second guest item 34B at the second location by presenting the respective unique identifier to be read by the particular input device 84 of the particular container 80.

Figure 5:
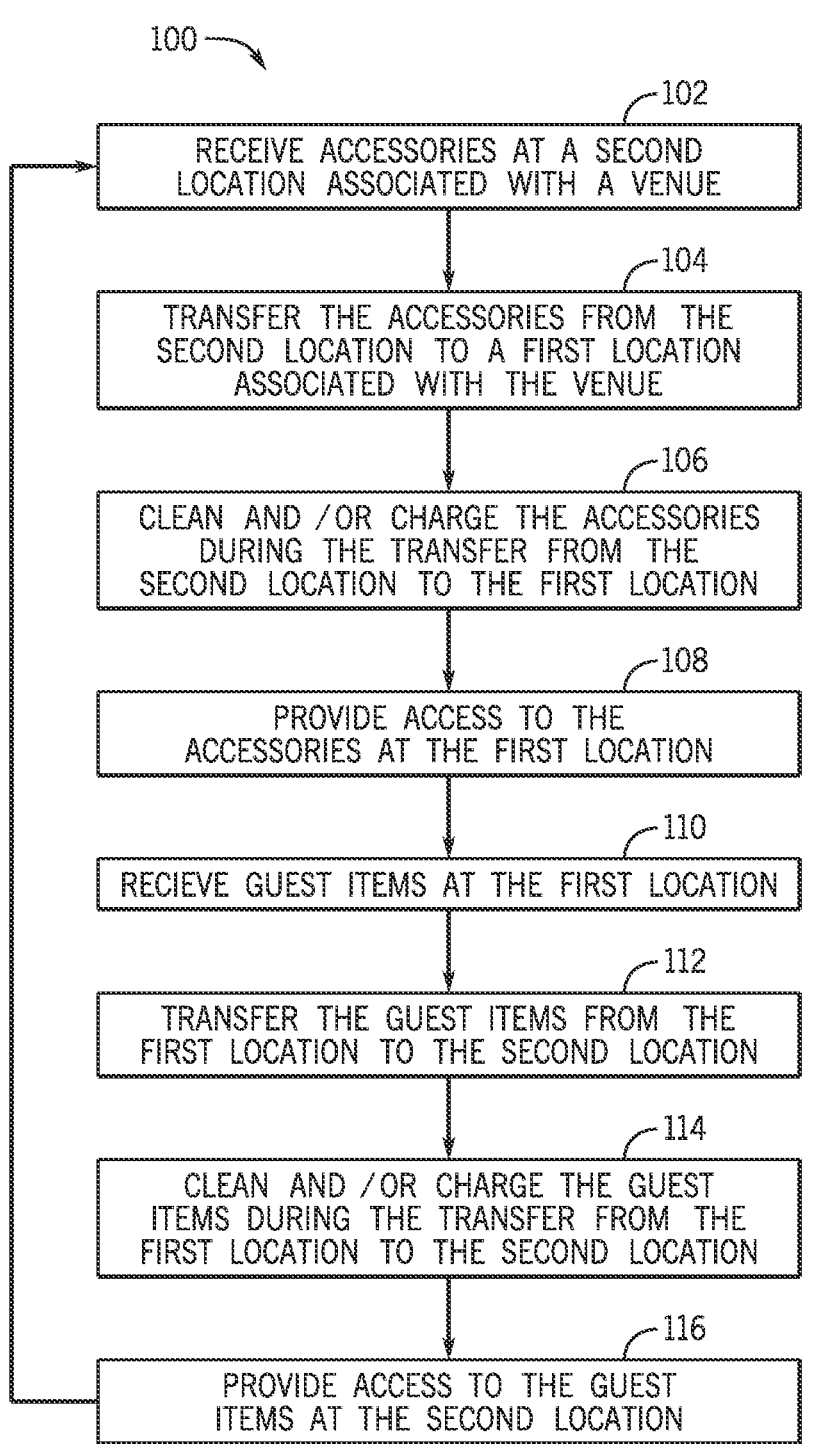
FIG. 5 is a flow diagram of a method of operating the cleaning and transferring system of FIG. 1, in accordance with an embodiment of the present disclosure.

FIG. 5 is a flow diagram of an embodiment of a method 100 of operating a cleaning and transferring system, such as the cleaning and transferring system 10 of FIG. 1. The following description of the method 100 is described as being performed by a system (e.g., the system 10), which may be controlled by a control system (e.g., the control system 70). Moreover, although the following description of the method 100 is described as including certain steps performed in a particular order, it should be understood that the steps of the method 100 may be performed in any suitable order, that certain steps may be omitted, and/or that certain steps may be added.

In block 102, the method 100 may include receiving one or more accessories at a second location associated with a venue (e.g., environment). For example, guests may place the one or more accessories on a conveyor of a system while the guests are present at the second location in the venue. In one embodiment, the second location in the venue may be located between an unloading zone of an attraction portion of the venue and an exit portion of the venue.

In block 104, the method 100 may include transferring the one or more accessories from the second location to a first location associated with the venue. For example, the conveyor may move (e.g., continuously or in intervals; in a loop) to carry the one or more accessories from the second location to the first location. In one embodiment, the first location in the venue may be located between an entrance portion of the venue and a loading zone of the attraction portion of the venue, at an entrance portion of the venue, or at a loading zone of the attraction portion of the venue.

In block 106, the method 100 may include cleaning and/or charging the one or more accessories during the transferring of the one or more accessories from the second location to the first location. For example, the system may include a cleaning device, and the conveyor may pass through the cleaning device to carry the one or more accessories through the cleaning device during the transferring of the one or more accessories from the second location to the first location. In one embodiment, the system may include a charging system, and the one or more accessories may receive power via contacts and/or charging pads on the conveyor during the transferring of the one or more accessories from the second location to the first location.

In block 108, the method 100 may include providing access to the one or more accessories at the first location. For example, guests may retrieve the one or more accessories on the conveyor of a system while the guests are present at the first location in the venue. Advantageously, when the guests retrieve the one or more accessories in this way, the one or more accessories may be clean and/or charged for use by the guests (e.g., via the cleaning and/or charging process at block 106).

In block 110, the method 100 may include receiving one or more guest items at the first location. For example, the guests may place the one or more guest items on the conveyor while the guests are present at the first location. The guests may pick up the one or more accessories (block 108) from the conveyor and deposit the one or more guest items onto the conveyor in sequence (e.g., one after the other) or at the same time.

In block 112, the method 100 may include transferring the one or more guest items from the first location to the second location. For example, the conveyor may move (e.g., continuously or in intervals; in the loop) to carry the one or more guest items from the first location to the second location.

In block 114, the method 100 may include cleaning and/or charging the one or more guest items during the transferring of the one or more guest items from the first location to the second location. For example, the system may include an additional cleaning device, and the conveyor may pass through the additional cleaning device to carry the one or more guest items through the additional cleaning device during the transferring of the one or more guest items from the first location to the second location. In one embodiment, the system may include the charging system, and the one or more guest items may receive power via contacts and/or charging pads on the conveyor during the transferring of the one or more guest items from the first location to the second location.

In block 116, the method 100 may include providing access to the one or more guest items at the second location. For example, the guests may retrieve the one or more guest items on the conveyor while the guests are present at the second location in the venue. Advantageously, when the guests retrieve the one or more guest items in this way, the one or more guest items may be clean and/or charged for use by the guests (e.g., via the cleaning and/or charging process at block 114).

Additionally, as described herein, the guests may experience the attraction portion of the environment while the system carries out operations set forth in blocks 110-116. Thus, the guests may not have to carry their own guest items into the attraction portion of the environment, which may provide more room in ride vehicles, free guests' hands to manipulate objects in the attraction portion of the environment (e.g., respective accessories picked up at the first location), and so forth. Additionally, the system (e.g., the conveyor, which may be a single, continuous loop structure) may simultaneously and efficiently clean the one or more accessories for use by multiple guests over time.

It should be appreciated that features shown and described with reference to FIGS. 1-5 may be combined in any suitable manner. While only certain features of the invention have been illustrated and described herein, many modifications and changes will occur to those skilled in the art. It is, therefore, to be understood that the appended claims are intended to cover all such modifications and changes as fall within the true spirit of the invention.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for (perform)ing (a function) . . . " or "step for (perform)ing (a function) . . . ", it is intended that such elements are to be interpreted under 35 U.S.C. 112 (f). However, for any claims containing elements designated in any other manner, it is intended that such elements are not to be interpreted under 35 U.S.C. 112 (f).

The invention claimed is:

1. A method of operating a system in a venue with a first location and a second location, the method comprising:
 receiving an accessory into a container on a conveyor at the second location;
 transferring the container containing the accessory from the second location to the first location via the conveyor;
 cleaning the accessory during the transferring of the container from the second location to the first location via the conveyor;
 receiving a personal guest item of a guest into an additional container on the conveyor at the first location;
 blocking access to the personal guest item received in the additional container via locking the additional container;
 transferring the additional container containing the personal guest item from the first location to the second location via the conveyor; and
 unlocking the additional container at the second location based on interfacing with the accessory, thereby allowing the personal guest item to be removed from the additional container.

2. The method of claim 1, comprising simultaneously:
 transferring the accessory from the second location to the first location in the venue via the conveyor, and
 transferring the personal guest item from the first location to the second location via the conveyor.

3. The method of claim 1, comprising cleaning the personal guest item during the transferring of the additional container containing the personal guest item from the first location to the second location via the conveyor.

4. The method of claim 3, comprising cleaning the personal guest item according to one or more inputs indicative of preferences of the guest.

5. The method of claim 1, wherein the first location is located between an entrance and an attraction portion of the venue, and the second location is located between the attraction portion and an exit of the venue.

6. The method of claim 1, comprising transferring the accessory from the second location to the first location via a first one-way conveyor that forms part of the conveyor, and transferring the personal guest item from the first location to the second location via a second one-way conveyor portion that forms part of the conveyor.

7. The method of claim 1, comprising charging the accessory during the transferring of the container containing the accessory from the second location to the first location via the conveyor.

8. The method of claim 1, comprising charging the personal guest item during the transferring of the additional container containing the personal guest item from the first location to the second location via the conveyor.

9. The method of claim 1, comprising adjusting a speed of the conveyor based on one or more inputs indicative of timing information from an attraction portion of the venue.

10. The method of claim 1, comprising setting a speed of the conveyor such that the personal guest item arrives at the second location as the guest reaches the second location after traveling from the first location and through an attraction experience in an attraction portion of the venue.

11. The method of claim 1, wherein the accessory is associated with a unique identifier, the method comprising:

receiving, at the additional container, the unique identifier associated with the accessory; and unlocking the additional container based on the unique identifier matching a stored identifier for the additional container.

* * * * *